US006573425B1

(12) United States Patent
Baszczynski et al.

(10) Patent No.: US 6,573,425 B1
(45) Date of Patent: Jun. 3, 2003

(54) COMPOSITIONS AND METHODS TO REDUCE THE COMPLEXITY OF TRANSGENE INTEGRATION IN THE GENOME OF A PLANT

(75) Inventors: Christopher L. Baszczynski, Urbandale, IA (US); Benjamin A. Bowen, Des Moines, IA (US); David J. Peterson, Ames, IA (US); Laura A. Tagliani, Ankeny, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/439,042

(22) Filed: Nov. 12, 1999

Related U.S. Application Data

(62) Division of application No. 09/193,502, filed on Nov. 17, 1998, now Pat. No. 6,187,994.
(60) Provisional application No. 60/065,627, filed on Nov. 18, 1997, and provisional application No. 60/065,613, filed on Nov. 18, 1997.

(51) Int. Cl.$^7$ .............................. A01H 1/00; A01H 5/00; C12N 15/82; C12N 15/87
(52) U.S. Cl. ........................ 800/278; 435/462; 435/468; 435/412; 435/415; 435/416; 435/419; 800/288; 800/306; 800/312; 800/314; 800/320; 800/320.1; 800/322
(58) Field of Search ........................ 800/21, 278, 288, 800/306, 312, 314, 320, 320.1, 322; 435/468, 455, 462, 412, 415, 416, 419; 536/24.2

(56) References Cited

U.S. PATENT DOCUMENTS

| | | | |
|---|---|---|---|
| 5,677,177 A | 10/1997 | Wahl et al. | 435/325 |
| 6,010,884 A | 1/2000 | Griffiths | 435/69.7 |
| 6,171,861 B1 | 1/2001 | Hartley et al. | 435/455 |
| 6,262,341 B1 | 7/2001 | Baszczynski et al. | 800/278 |
| 6,300,545 B1 | 10/2001 | Baszczynski et al. | 800/294 |
| 6,331,661 B1 | 12/2001 | Baszczynski et al. | 800/278 |

FOREIGN PATENT DOCUMENTS

| | | |
|---|---|---|
| WO | WO 92/15694 | 9/1992 |
| WO | WO 93/01283 | 1/1993 |
| WO | WO 93/17116 A1 | 9/1993 |
| WO | WO 94/17176 | 8/1994 |
| WO | WO 95/00555 | 1/1995 |
| WO | WO 96/04393 | 2/1996 |
| WO | WO 97/09436 | 3/1997 |
| WO | WO 97/09439 | 3/1997 |
| WO | WO 97/13401 | 4/1997 |
| WO | WO 97/37012 | 10/1997 |
| WO | WO 99/23202 | 5/1999 |
| WO | WO 99/55851 | 11/1999 |

OTHER PUBLICATIONS

Albert, H. et al., "Site–specific integration of DNA into wild–type and mutant lox sites placed in the plant genome." 1995, The Plant Journal, vol. 7, pp. 649–659.*
Lyznik, L. A. et al., "Activity of yeast FLP recombinase in maize and rice protoplasts." 1993, Nucleic Acids Research, vol. 21, pp. 969–975.*
Esposito, M. S. et al., "Recombinators, recombinases and recombination genes of yeast." 1994, Current Genetics, vol. 25, pp. 1–11.*
Lloyd, A.M., and R.W. Davis, "Functional Expression of the Yeast FLP/FRT Site–Specific Recombination System in *Nicotiana tabacum*," *Mol. Gen. Genet,* 1994, pp. 653–657, vol. 242.
Osborne, B., et al., "A System for Insertional Mutagenesis and Chromosomal Rearrangement Using the Ds Transposon and Cre–lox," *The Plant Journal,* 1995, pp. 687–701, vol. 7(4).
Karreman et al. (1996) "On the Use of Double FLP Recognition Targets (FRTs) in the LTR of Retroviruses for the Construction of high Producer Cell Lines", *Nucleic Acids Research* 24(9):1616–1624.
Storici et al. (1997) "Molecular Engineering with the FRT Sequence of the Yeast 2 μmPlasmid: [cir°] Segregant Enrichment by Counterselection for 2 μm Site–Specific Recombination",*Gene* 195:245–255.
Czakó et al. (1997) "Negative Selection Markers for Plants", Technology Transfer of Plant Biotechnology, Chapter 6, Edited by Peter M. Gresshoff, Plant Molecular Genetics, Institute of Agriculture, Center for Legume Research, The University of Tennessee, Knoxville, Tennessee, CRC Press, pp. 67–93.
Dasgupta et al. (1991) "Rice Tungro Bacilliform Virus DNA Independently Infects Rice AfterAgrobacterium–mediated Transfer", *Journal of General Virology* 721215–1221.
Grimsley et al. (1988) "Meristematic Tissues of Maize Plants are Most Susceptible to Agroinfection with Maize Streak Virus", *Bio/Technology* 6:185–189.
Louie (1995) "Vascular Puncture of Maize Kernels for the Mechanical Transmission of Maize White Line Mosaic Virus and Other Viruses of Maize", *Photopathology* 85(2):139–143.

(List continued on next page.)

*Primary Examiner*—David T. Fox
*Assistant Examiner*—David H Kruse
(74) *Attorney, Agent, or Firm*—Alston & Bird LLP

(57) ABSTRACT

Methods for reducing the complexity of integration of nucleotide sequences into a plant are provided. Transfer cassettes comprising nucleotide sequences of interest flanked by non-identical recombination sites are used to transform a plant comprising a target site. The target site contains at least a set of non-identical recombination sites corresponding to those on the transfer cassette. Exchange of the nucleotide sequences flanked by the recombination sites is effected by a recombinase.

37 Claims, 2 Drawing Sheets

OTHER PUBLICATIONS

Scholthof et al. (1996) "Plant Virus Gene Vectors For Transient Expression Of Foreign Proteins In Plants",*Annu. Rev. of Phytopathol. 34*:299–323.

Timmermans et al. (1992) "Trans Replication and High Copy Numbers of Wheat Dwarf Virus Vectors in Maize Cells", *Nucleic Acids Research 20(15)*:4047–4054.

Ugaki et al. (1991) "Replication of aGeminivirus Derived Shuttle Vector in Maize Endosperm Cells",*Nucleic Acids Research 19(2)*:371–377.

Snaith et al., Multiple Cloning Sites Carrying loxP and FRT Recognition Sites for the Cre and Flp Site–Specific Recombinases, Gene, 1995, pp. 173–174, vol. 166.

Ow et al., Genome Manipulation Through Site–Specific Recombination, Critical Reviews in Plant Sciences, (1995), pp. 239–261, vol. 14(3).

Senecoff et al. Directionality in FLP Protein–Promoted Site–Specific Recombination Is Mediated by DNA—DNA Pairing, *J. Biol. Chem.,* Jun. 5, 1986, pp. 7380–7386, vol. 261(16), The American Society of Biological Chemists, Inc., Madison, Wisconsin.

Senecoff et al., DNA Recognition by the FLP Recombinase of the Yeast $2\mu$ Plasmid: A Mutational Analysis of the FLP Binding Site, J. Mol. Biol., 1988, pp. 405–421, vol. 201, Academic Press, Ltd., USA.

Campbell et al., Codon Usage in Higher Plants, Green Algae, and Cyanobacteria, Plant Physiol., 1990, pp. 1–11, vol. 92, Houghton, Michigan.

O'Gorman et al. Recombinase–Mediated Gene Activation and Site–Specific Integration in Mammalian Cells, *Science,* Mar. 15, 1991, pp. 1351–1355, vol. 251, Salk Institute for Biological Studies, La Jolla, California.

Dale et al. Gene Transfer with Subsequent Removal of the Selection Gene From the Host Genome, *Proc. Natl. Acad. Sci. USA,* Dec. 1991, vol. 88, pp. 1058–10562, Plant Gene Expression Center, U.S. Department of Agriculture, Berkeley, California.

Sauer, Identification of Cryptic lox Sites in the Yeast Genome by Selection for Cre–mediated Chromosome Translocations that Confer Multiple Drug Resistance, J. Mol. Biol., 1992, pp. 911–928, vol. 223, Academic Press, Ltd., USA.

Russell et al. Directed Excision of a Transgene from the Plant Genome, *Mol. Genet.Genet.,* (1992), vol. 234, pp. 49–59, MGG Springer–Verlag.

Lyznik et al. Activity of Yeast FLP Recombinase in Maize and Rice Protoplasts, *Nuc. Acids Res.,* 1993, vol. 21(4), pp. 969–975, Oxford University Press.

Lyznik et al. Heat–Inducible Expression of FLP Gene in Maize Cells, *Plant J.,* 1995, vol. 8(2), pp. 177–186, Purdue University, West Lafayette, IN.

Kilby et al. FLP Recombinase in Transgenic Plants: Constitutive Activity in Stably Transformed Tobacco and Generation of Marked Cell Clones in Arabidopsis, *Plant J.,* 1995, vol. 8(5), pp. 637–652, University of Cambridge, Cambridge, UK.

Albert et al. Site–Specific Integration of DNA into Wild–Type and Mutant Lox Sites Placed in the Plant Genome, *Plant J.,* 1995, vol. 7(4), pp. 649–659, Plant Gene Expression Center, Albany, California.

Logie et al. Ligand–Regulated Site–Specific Recombination, *Proc. Natl. Acad. Sci. USA,* Jun. 1995), vol. 92, pp. 5940–5944, European Molecular Biology Laboratory, Heidelberg, Germany.

Zhang et al. Inducible Site–Directed Recombination in Mouse Embryonic Stem Cells, *Nuc. Acids Res.,* 1996, vol. 24(4), pp. 543–548, Oxford University Press.

Lyznik et al. FLP–Mediated Recombination of FRT Sites in the Maize Genome, *Nuc. Acids Res.* 1996, vol. 24(19), pp. 3784–3789, Oxford University Press.

Araki et al. Targeted Integration of DNA Using Mutant Lox Sites in Embryonic Stem Cells, *Nuc. Acids Res.,* 1997, vol. 25(4), pp. 868–872, Oxford University Press.

Bethke et al. Segmental Genomic Replacement by Cre–Mediated Recombination: Genotoxic Stress Activation of the p53 Promoter in Single–Copy Transformants, *Nuc. Acids Res.,* 1997, vol. 25(14), pp. 2828–2834, National Institutes of Health, National Institute of Diabetes, Digestive and Kidney Disease, Bethesda, Maryland.

Golic et al. FLP–Mediated DNA Mobilization to Specific Target Sites in Drosophila Chromosomes, *Nuc. Acids Res.,* 1997, vol. 25(18), pp. 3665–3671, Oxford University Press.

O'Gorman et al. Protamine–Cre Recombinase Transgenes Efficiently Recombine Target Seqences in the Male Germ Line of Mice, but Not in Embryonic Stem Cells, *Proc. Natl. Acad. Sci. USA,* Dec. 1997, vol. 94, pp. 14602–14607, Salk Institute for Biological Studies, Sand Diego, California.

Feil et al. Regulation of Cre Recombinase Activity by Mutated Estrogen Receptor Ligand–Binding Domains, *Biochem. Biophys. Res. Comm.,* 1997, vol. 237, pp. 752–757, Academic Press.

Seibler and Bode, Double–Reciprocal Crossover Mediated by FLP–Recombinase: A Concept and an Assay, Biochemistry, 1997, pp. 1740–1747, vol. 36(7).

Narasimhulu et al., Early Transcription of Agrobacterium T–DNA Genes in Tobacco and Maize, The Plant Cell, May 1996, pp. 873–886, vol. 8, American Society of Plant Physiologists.

McLeod et al. Identification of the Crossover Site During FLP–Mediated Recombination in the *Saccharomyces Cerevisiae* Plasmid 2 $\mu$m Circle, *Mol. Cell. Biol.,* Oct., 1986, pp. 3357–3367, vol. 6(10), American Society for Microbiology, Cold Spring Harbor, New York.

Schlake et al. Use of Mutated FLP Recognition Target (FRT) Sites for the Exchange of Expression Cassettes at Defined Chromosomal Loci, *Biochem.,* 1994, vol. 33(43), pp. 12746–12751, American Chemical Society.

* cited by examiner

COMPOSITIONS AND METHODS TO REDUCE THE COMPLEXITY OF TRANSGENE INTEGRATION IN THE GENOME OF A PLANT

CROSS-REFERENCE TO RELATED APPLICATIONS

This application is a divisional of U.S. application Ser. No. 09/193,502, filed Nov. 17, 1998, now U.S. Pat. No. 6,187,994 published Feb. 13, 2001, which claims the benefit of U.S. Provisional Application Ser. No. 60/065,627, filed Nov. 18, 1997 and U.S. Provisional Application Ser. No. 60/065,613 filed Nov. 18, 1997, all of which are herein incorporated by reference.

FIELD OF THE INVENTION

The invention relates to the genetic modification of plants. Particularly, the control of gene integration and expression in plants is provided.

BACKGROUND OF THE INVENTION

Genetic modification techniques enable one to insert exogenous nucleotide sequences into an organism's genome. A number of methods have been described for the genetic modification of plants. All of these methods are based on introducing a foreign DNA into the plant cell, isolation of those cells containing the foreign DNA integrated into the genome, followed by subsequent regeneration of a whole plant. Unfortunately, such methods produce transformed cells that contain the introduced foreign DNA inserted randomly throughout the genome and often in multiple copies.

The random insertion of introduced DNA into the genome of host cells can be lethal if the foreign DNA happens to insert into, and thus mutate, a critically important native gene. In addition, even if a random insertion event does not impair the functioning of a host cell gene, the expression of an inserted foreign gene may be influenced by "position effects" caused by the surrounding genomic DNA. In some cases, the gene is inserted into sites where the position effects are strong enough to prevent the synthesis of an effective amount of product from the introduced gene. In other instances, overproduction of the gene product has deleterious effects on the cell.

Transgene expression is typically governed by the sequences, including promoters and enhancers, which are physically linked to the transgene. Currently, it is not possible to precisely modify the structure of transgenes once they have been introduced into plant cells. In many applications of transgene technology, it would be desirable to introduce the transgene in one form, and then be able to modify the transgene in a defined manner. By this means, transgenes could be activated or inactivated where the sequences that control transgene expression can be altered by either removing sequences present in the original transgene or by inserting additional sequences into the transgene.

For higher eukaryotes, homologous recombination is an essential event participating in processes like DNA repair and chromatid exchange during mitosis and meiosis. Recombination depends on two highly homologous extended sequences and several auxiliary proteins. Strand separation can occur at any point between the regions of homology, although particular sequences may influence efficiency. These processes can be exploited for a targeted integration of transgenes into the genome of certain cell types.

Even with the advances in genetic modification of higher plants, the major problems associated with the conventional gene transformation techniques have remained essentially unresolved as to the problems discussed above relating to variable expression levels due to chromosomal position effects and copy number variation of transferred genes. For these reasons, efficient methods are needed for targeting and control of insertion of nucleotide sequences to be integrated into a plant genome.

SUMMARY OF THE INVENTION

Compositions and methods for the targeted integration of nucleotide sequences into a transformed plant are provided. The compositions comprise transfer cassettes which are flanked by non-identical recombination sites.

The methods find use in targeting the integration of nucleotide sequences of interest to a specific chromosomal site, finding optimal integration sites in a plant genome, comparing promoter activity in transformed plants, engineering chromosomal rearrangements, and other genetic manipulation of plants.

Novel minimal recombination sites (FRT) are provided for use in the methods of the invention. Also provided are targeting cassettes and transgenic plants and plant cells containing corresponding non-identical recombination sites.

DETAILED DESCRIPTION OF THE INVENTION

Figure 1:
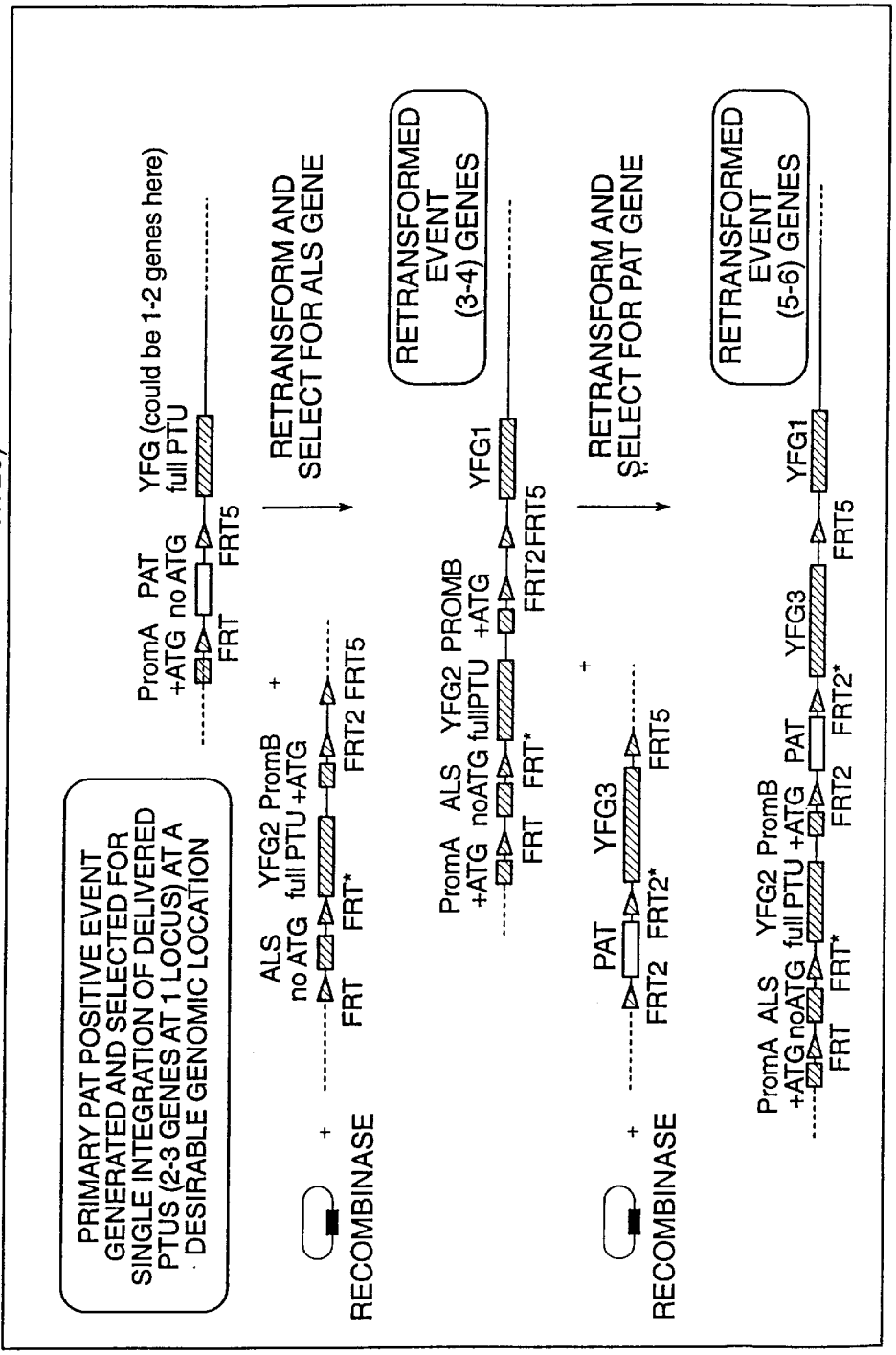
FIG. 1 provides one scheme for gene stacking via site-specific integration using the FLP system.

Compositions and methods for the directional, targeted integration of exogenous nucleotides into a transformed plant are provided. The methods use novel recombination sites in a gene targeting system which facilitates directional targeting of desired genes and nucleotide sequences into corresponding recombination sites previously introduced into the target plant genome.

In the methods of the invention, a nucleotide sequence flanked by two non-identical recombination sites is introduced into the target organism's genome establishing a target site for insertion of nucleotide sequences of interest. Once a stable plant or cultured tissue is established a second construct, or nucleotide sequence of interest, flanked by corresponding recombination sites as those flanking the target site, is introduced into the stably transformed plant or tissues in the presence of a recombinase protein. This process results in exchange of the nucleotide sequences between the non-identical recombination sites of the target site and the transfer cassette.

It is recognized that the transformed plant may comprise multiple target sites; i.e., sets of non-identical recombination sites. In this manner, multiple manipulations of the target site in the transformed plant are available. By target site in the transformed plant is intended a DNA sequence that has been inserted into the transformed plant's genome and comprises non-identical recombination sites.

Examples of recombination sites for use in the invention are known in the art and include FRT sites (See, for example, Schlake and Bode (1994) *Biochemistry* 33:12746–12751; Huang et al. (1991) *Nucleic Acids Research* 19:443–448; Paul D. Sadowski (1995) In Progress in Nucleic Acid Research and Molecular Biology vol. 51, pp. 53–91; Michael M. Cox (1989) In Mobile DNA, Berg and Howe (eds) American Society of Microbiology, Washington D.C., pp. 116–670; Dixon et al. (1995) 18:449–458; Umlauf and Cox (1988) The EMBO Journal 7:1845–1852; Buchholz et al. (1996) Nucleic Acids Research 24:3118–3119; Kilby et al. (1993) Trends Genet. 9:413–421: Rossant and Geagy (1995) Nat. Med. 1: 592–594; Albert et al. (1995) The Plant J. 7:649–659: Bayley et al. (1992) Plant Mol. Biol. 18:353–361; Odell et al. (1990) Mol. Gen. Genet. 223:369–378; and Dale and Ow (1991) Proc. Natl. Acad. Sci. USA 88:10558–105620; all of which are herein incorporated by reference.); Lox (Albert et al. (1995) Plant J. 7:649–659; Qui et al. (1994) Proc. Natl. Acad. Sci. USA 91:1706–1710; Stuurman et al. (1996) Plant Mol. Biol. 32:901–913; Odell et al. (1990) Mol. Gen. Gevet. 223:369–378; Dale et al. (1990) Gene 91:79–85; and Bayley et al. (1992) Plant Mol. Biol. 18:353–361.)

The two-micron plasmid found in most naturally occurring strains of Saccharomyces cerevisiae, encodes a site-specific recombinase that promotes an inversion of the DNA between two inverted repeats. This inversion plays a central role in plasmid copy-number amplification. The protein, designated FLP protein, catalyzes site-specific recombination events. The minimal recombination site (FRT, SEQ ID NO 1) has been defined and contains two inverted 13-base pair (bp) repeats surrounding an asymmetric 8-bp spacer. The FLP protein cleaves the site at the junctions of the repeats and the spacer and is covalently linked to the DNA via a 3' phosphate.

Site specific recombinases like FLP cleave and religate DNA at specific target sequences, resulting in a precisely defined recombination between two identical sites. To function, the system needs the recombination sites and the recombinase. No auxiliary factors are needed. Thus, the entire system can be inserted into and function in plant cells.

The yeast FLP\FRT site specific recombination system has been shown to function in plants. To date, the system has been utilized for excision of unwanted DNA. See, Lyznik et at. (1993) Nucleic Acid Res. 21:969–975. In contrast, the present invention utilizes non-identical FRTs for the exchange, targeting, arrangement, insertion and control of expression of nucleotide sequences in the plant genome.

To practice the methods of the invention, a transformed organism of interest, particularly a plant, containing a target site integrated into its genome is needed. The target site is characterized by being flanked by non-identical recombination sites. A targeting cassette is additionally required containing a nucleotide sequence flanked by corresponding non-identical recombination sites as those sites contained in the target site of the transformed organism. A recombinase which recognizes the non-identical recombination sites and catalyzes site-specific recombination is required.

It is recognized that the recombinase can be provided by any means known in the art. That is, it can be provided in the organism or plant cell by transforming the organism with an expression cassette capable of expressing the recombinase in the organism, by transient expression; or by providing messenger RNA (mRNA) for the recombinase or the recombinase protein.

By "non-identical recombination sites" is intended that the flanking recombination sites are not identical in sequence and will not recombine or recombination between the sites will be minimal. That is, one flanking recombination site may be a FRT site where the second recombination site may be a mutated FRT site. The non-identical recombination sites used in the methods of the invention prevent or greatly suppress recombination between the two flanking recombination sites and excision of the nucleotide sequence contained therein. Accordingly, it is recognized that any suitable non-identical recombination sites may be utilized in the invention, including FRT and mutant FRT sites, FRT and lox sites, lox and mutant lox sites, as well as other recombination sites known in the art.

By suitable non-identical recombination site implies that in the presence of active recombinase, excision of sequences between two non-identical recombination sites occurs, if at all, with an efficiency considerably lower than the recombinationally-mediated exchange targeting arrangement of nucleotide sequences into the plant genome. Thus, suitable non-identical sites for use in the invention include those sites where the efficiency of recombination between the sites is low; for example, where the efficiency is less than about 30 to about 50%, preferably less than about 10 to about 30%, more preferably less than about 5 to about 10%.

As noted above, the recombination sites in the targeting cassette correspond to those in the target site of the transformed plant. That is, if the target site of the transformed plant contains flanking non-identical recombination sites of FRT and a mutant FRT, the targeting cassette will contain the same FRT and mutant FRT non-identical recombination sites.

It is furthermore recognized that the recombinase, which is used in the invention, will depend upon the recombination sites in the target site of the transformed plant and the targeting cassette. That is, if FRT sites are utilized, the FLP recombinase will be needed. In the same manner, where lox sites are utilized, the Cre recombinase is required. If the non-identical recombination sites comprise both a FRT and a lox site, both the FLP and Cre recombinase will be required in the plant cell.

The FLP recombinase is a protein that catalyzes a site-specific reaction that is involved in amplifying the copy number of the two micron plasmid of S. cerevisiae during DNA replication. FLP protein has been cloned and expressed. See, for example, Cox (1993) Proc. Natl. Acad. Sci. U.S.A. 80:4223–4227. The FLP recombinase for use in the invention may be that derived from the genus Saccharomyces. It may be preferable to synthesize the recombinase using plant preferred codons for optimum expression in a plant of interest. See, for example, U.S. application Ser. No. 08/972,258 filed Nov. 18, 1997, entitled "Novel Nucleic Acid Sequence Encoding FLP Recombinase" now U.S. Pat. No. 5,929,301, herein incorporated by reference.

The bacteriophage recombinase Cre catalyzes site-specific recombination between two lox sites. The Cre recombinase is known in the art. See, for example, Guo et al. (1997) Nature 389:40–46; Abremski et al. (1984) J. Biol. Chem. 259:1509–1514; Chen et al. (1996) Somat. Cell Mol. Genet. 22:477–488; and Shaikh et al. (1977) J. Biol. Chem. 272:5695–5702. All of which are herein incorporated by reference. Such Cre sequence may also be synthesized using plant preferred codons.

Where appropriate, the nucleotide sequences to be inserted in the plant genome may be optimized for increased expression in the transformed plant. Where mammalian, yeast, or bacterial genes are used in the invention, they can be synthesized using plant preferred codons for improved expression. It is recognized that for expression in monocots, dicot genes can also be synthesized using monocot preferred codons. Methods are available in the art for synthesizing plant preferred genes. See, for example, U.S. Pat. Nos.

5,380,831, 5,436,391, and Murray et al. (1989) *Nucleic Acids Res.* 17:477–498, herein incorporated by reference.

The plant preferred codons may be determined from the codons utilized more frequently in the proteins expressed in the plant of interest. It is recognized that monocot or dicot preferred sequences may be constructed as well as plant preferred sequences for particular plant species. See, for example, EPA 0359472; EPA 0385962; WO 91/16432; Perlak et al. (1991) *Proc. Natl. Acad. Sci. USA*, 88:3324–3328; and Murray et al. (1989) *Nucleic Acids Research*, 17: 477–498. U.S. Pat. Nos. 5,380,831; 5,436,391; and the like, herein incorporated by reference. It is further recognized that all or any part of the gene sequence may be optimized or synthetic. That is, fully optimized or partially optimized sequences may also be used.

Additional sequence modifications are known to enhance gene expression in a cellular host and can be used in the invention. These include elimination of sequences encoding spurious polyadenylation signals, exon-intron splice site signals, transposon-like repeats, and other such well-characterized sequences, which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The present invention also encompasses novel FLP recombination target sites (FRT). The FRT (SEQ ID NO 1) has been identified as a minimal sequence comprising two 13 base pair repeats, separated by an 8 base spacer, as follows:

5'-GAAGTTCCTATTC[TCTAGAAA]
GTATAGGAACTTC3' wherein the nucleotides within the brackets indicate the spacer region. The nucleotides in the spacer region can be replaced with a combination of nucleotides, so long as the two 13-base repeats are separated by eight nucleotides. It appears that the actual nucleotide sequence of the spacer is not critical, however for the practice of the invention, some substitutions of nucleotides in the space region may work better than others.

The eight base pair spacer is involved in DNA-DNA pairing during strand exchange. The asymmetry of the region determines the direction of site alignment in the recombination event, which will subsequently lead to either inversion or excision. As indicated above, most of the spacer can be mutated without a loss of function. See, for example, Schlake and Bode (1994) Biochemistry 33:12746–12751, herein incorporated by reference.

Novel FRT mutant sites are provided for use in the practice of the methods of the present invention. Such mutant sites may be constructed by PCR-based mutagenesis. While mutant FRT sites (SEQ ID Nos 2, 3, 4 and 5) are provided herein, it is recognized that other mutant FRT sites may be used in the practice of the invention. The present invention is not the use of a particular FRT or recombination site, but rather that non-identical recombination sites or FRT sites can be utilized for targeted insertion and expression of nucleotide sequences in a plant genome. Thus, other mutant FRT sites can be constructed and utilized based upon the present disclosure.

As discussed above, bringing genomic DNA containing a target site with non-identical recombination sites together with a vector containing a transfer cassette with corresponding non-identical recombination sites, in the presence of the recombinase, results in recombination. The nucleotide sequence of the transfer cassette located between the flanking recombination sites is exchanged with the nucleotide sequence of the target site located between the flanking recombination sites. In this manner, nucleotide sequences of interest may be precisely incorporated into the genome of the host.

It is recognized that many variations of the invention can be practiced. For example, target sites can be constructed having multiple non-identical recombination sites. Thus, multiple genes or nucleotide sequences can be stacked or ordered at precise locations in the plant genome. Likewise, once a target site has been established within the genome, additional recombination sites may be introduced by incorporating such sites within the nucleotide sequence of the transfer cassette and the transfer of the sites to the target sequence. Thus, once a target site has been established, it is possible to subsequently add sites, or alter sites through recombination.

Another variation includes providing a promoter or transcription initiation region operably linked with the target site in an organism. Preferably, the promoter will be 5' to the first recombination site. By transforming the organism with a transfer cassette comprising a coding region, expression of the coding region will occur upon integration of the transfer cassette into the target site. This embodiment provides for a method to select transformed cells, particularly plant cells, by providing a selectable marker sequence as the coding sequence.

Other advantages of the present system include the ability to reduce the complexity of integration of trans-genes or transferred DNA in an organism by utilizing transfer cassettes as discussed above and selecting organisms with simple integration patterns. In the same manner, preferred sites within the genome can be identified by comparing several transformation events. A preferred site within the genome includes one that does not disrupt expression of essential sequences and provides for adequate expression of the transgene sequence.

The methods of the invention also provide for means to combine multiple cassettes at one location within the genome. See, for example, FIG. 1. Recombination sites may be added or deleted at target sites within the genome.

Any means known in the art for bringing the three components of the system together may be used in the invention. For example, a plant can be stably transformed to harbor the target site in its genome. The recombinase may be transiently expressed or provided. Alternatively, a nucleotide sequence capable of expressing the recombinase may be stably integrated into the genome of the plant. In the presence of the corresponding target site and the recombinase, the transfer cassette, flanked by corresponding non-identical recombination sites, is inserted into the transformed plant's genome.

Alternatively, the components of the system may be brought together by sexually crossing transformed plants. In this embodiment, a transformed plant, parent one, containing a target site integrated in its genome can be sexually crossed with a second plant, parent two, that has been genetically transformed with a transfer cassette containing flanking non-identical recombination sites, which correspond to those in plant one. Either plant one or plant two contains within its genome a nucleotide sequence expressing recombinase. The recombinase may be under the control of a constitutive or inducible promoter.

Inducible promoters include heat-inducible promoters, estradiol-responsive promoters, chemical inducible promoters, and the like. Pathogen inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *The Plant Cell* 4:645–656; and Van Loon (1985) *Plant Mol. Virol.* 4:111–116. In this manner, expression of recombinase and subsequent activity at the recombination sites can be controlled.

Constitutive promoters for use in expression of genes in plants are known in the art. Such promoters include, but are not limited to 35S promoter of cauliflower mosaic virus (Depicker et al. (1982) *Mol. Appl. Genet.* 1:561–573; Odell et al. (1985) *Nature* 313:810–812), ubiquitin promoter (Christensen et al. (1992) *Plant Mol. Biol.* 18:675–689), promoters from genes such as ribulose bisphosphate carboxylase (De Almeida et al. (1989) *Mol. Gen. Genet.* 218:78–98), actin (McElroy et al. (1990) *Plant J.* 2:163–171), histone, DnaJ (Baszczynski et al. (1997) Maydica 42:189–201), and the like.

The compositions and methods of the invention find use in targeting the integration of transferred nucleotide sequences to a specific chromosomal site. The nucleotide sequence may encode any nucleotide sequence of interest. Particular genes of interest include those which provide a readily analyzable functional feature to the host cell and/or organism, such as marker genes, as well as other genes that alter the phenotype of the recipient cells, and the like. Thus, genes effecting plant growth, height, susceptibility to disease, insects, nutritional value, and the like may be utilized in the invention. The nucleotide sequence also may encode an 'antisense' sequence to turn off or modify gene expression.

It is recognized that the nucleotide sequences will be utilized in a functional expression unit or cassette. By functional expression unit or cassette is intended, the nucleotide sequence of interest with a functional promoter, and in most instances a termination region. There are various ways to achieve the functional expression unit within the practice of the invention. In one embodiment of the invention, the nucleic acid of interest is transferred or inserted into the genome as a functional expression unit. Alternatively, the nucleotide sequence may be inserted into a site within the genome which is 3' to a promoter region. In this latter instance, the insertion of the coding sequence 3' to the promoter region is such that a functional expression unit is achieved upon integration. For convenience, for expression in plants, the nucleic acid encoding target sites and the transfer cassettes, including the nucleotide sequences of interest, can be contained within expression cassettes. The expression cassette will comprise a transcriptional initiation region, or promoter, operably linked to the nucleic acid encoding the peptide of interest. Such an expression cassette is provided with a plurality of restriction sites for insertion of the gene or genes of interest to be under the transcriptional regulation of the regulatory regions.

The transcriptional initiation region, the promoter, may be native or homologous or foreign or heterologous to the host, or could be the natural sequence or a synthetic sequence. By foreign is intended that the transcriptional initiation region is not found in the wild-type host into which the transcriptional initiation region is introduced. Either a native or heterologous promoter may be used with respect to the coding sequence of interest.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the potato proteinase inhibitor (PinII) gene or from Ti-plasmid of *A. tumefaciens*, such as the octopine synthase and nopaline synthase termination regions. See also, Guerineau et al., (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA,* 86:6126–6130); potyvirus leaders, for example, TEV leader (Tobacco Etch Virus) (Allison et al. (1986); MDMV leader (Maize Dwarf Mosaic Virus); *Virology,* 154:9–20), and human immunoglobulin heavy-chain binding protein (BiP), (Macejak, D. G., and P. Sarnow (1991) *Nature,* 353:90–94; untranslated leader from the coat protein mRNA of alfalfa mosaic virus (AMV RNA 4), (Jobling, S. A., and Gehrke, L., (1987) *Nature,* 325:622–625; tobacco mosaic virus leader (TMV), (Gallie et al. (1989) *Molecular Biology of RNA, pages* 237–256, Gallie et al. (1987) *Nucl. Acids Res.* 15:3257–3273; and maize chlorotic mottle virus leader (MCMV) (Lommel, S. A. et al. (1991) *Virology,* 81:382–385). See also, Della-Cioppa et al. (1987) *Plant Physiology,* 84:965–968. Other methods known to enhance translation can also be utilized, for example, introns, and the like.

The expression cassettes may contain one or more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells. Selectable marker genes are utilized for the selection of transformed cells or tissues.

See generally, G. T. Yarranton (1992) *Curr. Opin. Biotech.,* 3:506–511; Christopherson et al. (1992) *Proc. Natl. Acad. Sci. USA,* 89:6314–6318; Yao et al. (1992) *Cell,* 71:63–72; W. S. Reznikoff (1992) *Mol. Microbiol.,* 6:2419–2422; Barkley et al. (1980) *The Operon, pp.* 177–220; Hu et al. (1987) *Cell,* 48:555–566; Brown et al. (1987) *Cell,* 49:603–612; Figge et al. (1988) *Cell,* 52:713–722; Deuschle et al. (1989) *Proc. Natl. Acad. Aci. USA,* 86:5400–5404; Fuerst et al. (1989) *Proc. Natl. Acad. Sci. USA,* 86:2549–2553; Deuschle et al. (1990) *Science,* 248:480–483; M. Gossen (1993) PhD Thesis, University of Heidelberg; Reines et al. (1993) *Proc. Natl. Acad. Sci. USA,* 90:1917–1921; Labow et al. (1990) *Mol. Cell Bio.,* 10:3343–3356; Zambretti et al. (1992) *Proc. Natl. Acad. Sci. USA,* 89:3952–3956; Baim et al. (1991) *Proc. Natl. Acad. Sci. USA,* 88:5072–5076; Wyborski et al. (1991) *Nuc. Acids Res.,* 19:4647–4653; A. Hillenand-Wissman (1989) *Topics in Mol. and Struc. Biol.,* 10:143–162; Degenkolb et al. (1991) *Antimicrob. Agents Chemother.,* 35:1591–1595; Kleinschnidt et al. (1988) *Biochemistry,* 27:1094–1104; Gatz et al. (1992) *Plant J.,* 2:397–404; A. L. Bonin (1993) PhD Thesis, University of Heidelberg; Gossen et al. (1992)

*Proc. Natl. Acad. Sci. USA,* 89:5547–5551; Oliva et al. (1992) *Antimicrob. Agents Chemother.,* 36:913–919; Hlavka et al. (1985) *Handbook of Exp. Pharmacology,* 78; Gill et al. (1988) Nature 334:721–724. Such disclosures are herein incorporated by reference.

Figure 2:
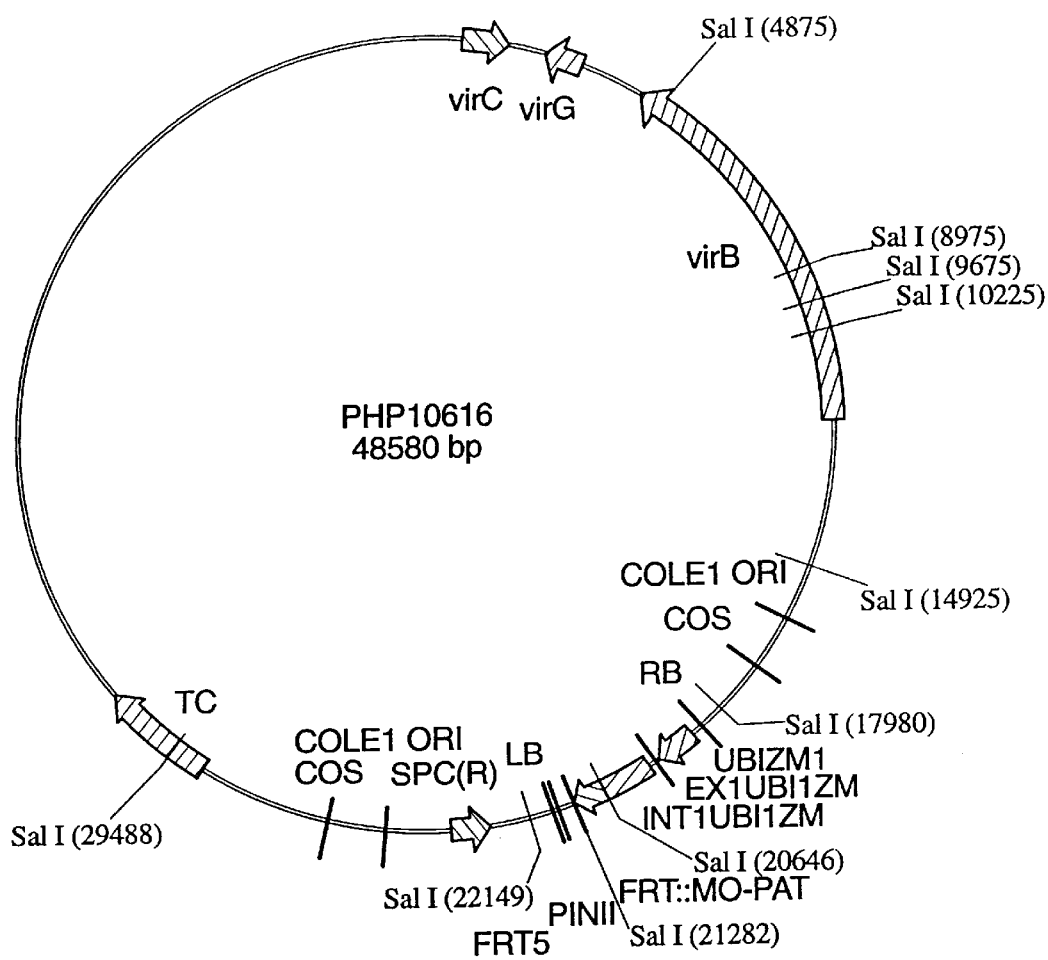
FIG. 2 provides a construct of the representative plasmid PHP10616.

The methods of the invention can also be utilized to find optimal integration sites within a plant genome. In this manner, a plant is transformed with an expression cassette comprising a selectable marker gene. The expression cassette is a target site as the marker gene is flanked by non-identical recombination sites. Transformed protoplast, tissues, or whole plants can be tested to determine the levels of activity of the inserted gene. By comparison of cellular activities of the gene in different insertion sites, preferred integration sites may be found wherein the gene is expressed at high or acceptable levels. These plants can then be utilized with subsequent retargeting techniques to replace the marker gene with other genes or nucleotide sequences of interest. In the same manner, multiple genes may be inserted at the optimal site for expression. See, for example, FIG. 2 which sets forth one scheme for gene stacking utilizing site-specific integration using the FRT/FLP system.

A variety of genetic manipulations are available using the compositions of the present invention including, for example, comparing promoter activity in a transformed plant. Prior to the present invention, promoter activity could not accurately be assessed and compared because the chimeric genes were inserted at different locations within the plant genome. Such chromosomal locations affected activity. By utilizing the methods of the present invention, a direct comparison of promotor activity in a defined chromosomal context is possible. Thus, using the methods, enhanced activity of genes can be achieved by selecting optimal chromosomal sites as well as optimal promoters for expression in the plant cell.

The present invention may be used for transformation of any plant species, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.) and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (Abies balsamea); and cedars such as Western red cedar (*Thuja plicata*) and Alaska yellow-cedar (*Chamaecyparis nootkatensis*). Preferably, plants of the present invention are crop plants (for example, corn, alfalfa, sunflower, canola, soybean, cotton, peanut, sorghum, wheat, tobacco, etc.), more preferably corn and soybean plants, yet more preferably corn plants.

It is recognized that the methods of the invention may be applied in any plant system. Methods for transformation of plants are known in the art. In this manner, genetically modified plants, plant cells, plant tissue, seed, and the like can be obtained. Transformation protocols may vary depending on the type of plant or plant cell, i.e., monocot or dicot, targeted for transformation. Suitable methods of transforming plant cells include microinjection (Crossway et al. (1986) Biotechniques 4:320–334), electroporation (Riggs et al. (1986) *Proc. Natl. Acad. Sci. USA,* 83:5602–5606, Agrobacterium mediated transformation (Hinchee et al. (1988) *Biotechnology,* 6:915–921), direct gene transfer (Paszkowski et al. (1984) *EMBO J.,* 3:2717–2722), and ballistic particle acceleration (see, for example, Sanford et al., U.S. Pat. No. 4,945,050; WO91/10725 and McCabe et al. (1988) *Biotechnology,* 6:923–926). Also see, Weissinger et al. (1988) *Annual Rev. Genet.,* 22:421–477; Sanford et al. (1987) *Particulate Science and Technology,* 5:27–37 (onion); Christou et al. (1988) *Plant Physiol.* 87:671–674 (soybean); McCabe et al. (1988) *Bio/Technology,* 6:923–926 (soybean); Datta et al. (1990) *Biotechnology,* 8:736–740 (rice); Klein et al. (1988) *Proc. Natl. Acad. Sci. USA,* 85:4305–4309(maize); Klein et al. (1988) *Biotechnology,* 6:559–563 (maize); WO9 1/10725 (maize); Klein et al. (1988) *Plant Physiol.,* 91:440–444(maize); Fromm et al. (1990) *Biotechnology,* 8:833–839; and Gordon-Kamm et al. (1990) *Plant Cell,* 2:603–618 (maize); Hooydaas-Van Slogteren & Hooykaas (1984) *Nature* (*London*), 311:763–764; Bytebier et al. (1987) *Proc. Natl. Acad. Sci. USA,* 84:5345–5349 (Liliaceae); De Wet et al. (1985) In *The Experimental Manipulation of Ovule Tissues,* ed. G. P. Chapman et al., pp. 197–209. Longman, NY (pollen); Kaeppler et al. (1990) *Plant Cell Reports,* 9:415–418; and Kaeppler et al. (1992) *Theor. Appl. Genet.,* 84:560–566 (whisker-mediated transformation); D'Halluin et al. (1992) *Plant Cell,* 4:1495–1505 (electroporation); Li et al. (1993) *Plant Cell Reports,* 12:250–255 and Christou and Ford (1995) *Annals of Botany,* 75:407–413 (rice); Osjoda et al. (1996) *Nature Biotechnology,* 14:745–750 (maize via *Agrobacterium tumefaciens*); all of which are herein incorporated by reference.

The cells which have been transformed may be grown into plants in accordance with conventional approaches. See, for example, McCormick et al. (1986) *Plant Cell Reports,* 5:81–84. These regenerated plants may then be pollinated with either the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

It is recognized that any means of transformation may be utilized for the present invention. However, for inserting the target site within the transformed plant, Agrobacterium-mediated transformation may be preferred. Agrobacterium-mediated transformation generally tends to insert a lower copy number of transferred DNA than does particle bombardment or other transformation means.

The following examples are offered by way of illustration and not by way of limitation.

Experimental

The general present invention provides a procedure for using existing and novel FRT sites in a new gene targeting system which facilitates directional retargeting of desired genes into FRT sites previously introduced in the target organism's genome. The novel FRT sites differ from previously described FRT sites in the sequence of the 8 bp spacer regions of the FRT sites. Previous publications also have shown that in the presence of FLP protein, recombination of sequences between two FRT sites occurs efficiently only with two identical FRT sites. See for example Umlauf and Cox (1988) *Embo J.* 7:1845–1852; Schlake and Bode (1994) *Biochem.* 33:12746–12751. To use the invention, a gene or DNA sequence is flanked by two non-identical FRT sites and introduced into a target organism's genome. The enclosed gene can be a selectable marker, thereby allowing selection for successfully introduced sequences. Molecular characterization confirms integration of desired sequences including complete FRT sites. Listed below are generic examples of vector constructions useful in practicing the invention:

A. FRTa-P1-G1-T1-FRTb
B. FRTa-P1-G1-T1-FRTa
C. FRTh-P1-G1-T1-FRTb
D. P1-FRTa-G1-T1-FRTb
E. P1-FRTa-G1-T1-FRTa
F. P1-FRTb-G1-T1-FRTb
G. P1-ATG::FRTa::G1(noATG)-T1-P2-G2-T2-FRTb
H. P1-ATG::FRTa::G1(noATG)-T1-P2-G2-T2-FRTb-P3-G3-T3
I. P1-ATG::FRTa::G1(noATG)-T1-FRTa::G2(noATG)-T2-FRTb
J. P1-ATG::FRTa::G1(noATG)-T1-FRTa::G2(noATG)-T2-FRTb-P3-G3-T3
K. P1-FRTa-G1-T1-P2-G2-T2-FRTb
L. P1-FRTa-G1-T1-P2-G2-T2-FRTb-P3-G3-T3
M. P1-FRTa-G1-T1-FRTa-G2-T2-FRTb
N. P1-FRTa-G1-T1-FRTa-G2-T2-FRTb-P3-G3-T3

Variations thereof may be constructed with other promoters, genes, terminators or FRT sites.

FRTa and FRTb are two examples of non-identical FRT sites. P1, P2 and P3 are different promoters, G1, G2, and G3 are different genes, T1, T2 and T3 are different terminators. ATG is the start of translation codon for the subsequent gene. The designation noATG indicates that particular gene is devoid of the ATG translation start codon. The symbol :: implies a fusion between adjacent elements, and where used between ATG, FRT and a gene, implies that the sequences are put together to generate an in frame translation fusion that results in a properly expressed and functional gene product.

A to F are preferred configurations for testing new FRT sites for ability to recombine sequences between them; the desired situation being that when two of the same site are used, recombination is efficient and that when two different sites are used, no recombination between them takes place in the presence of FLP protein. G to J are preferred configurations for general use in developing lines for retargeting. It is understood that any number of genes or other combinations of sequences can be assembled for use as part of this invention. K to N are possible configurations that could be used also.

Once a stable plant or cultured tissue is established with one of the constructs above, a second construct flanked by the same FRT sites used to flank the sequences in the first construct above is introduced into the stably transformed tissues in conjunction with the expression of FLP protein. The new vector constructs can be, but are not limited to the following:

O. FRTa::G1(noATG)-T1-FRTb
P. FRTa::G1(noATG)-T1-P2-G2-T2-FRTb
Q. FRTa-G1-T1-FRTb
R. FRTa-G1-T1-P2-G2-T2-FRTb

The FLP protein can be supplied by a) co-transforming with a plasmid carrying a gene encoding FLP; b) co-introducing FLP mRNA or protein directly; c) using a line for the initial transformation that expresses FLP either constitutively or following induction; or d) growing out the plants carrying the initial targeted vectors, crossing to plants that express active FLP protein and selecting events in the progeny.

As a working example, sequence O above is introduced into a line containing a copy of sequence G stably integrated in the genome, in the presence of functional FLP protein. Recombination takes place between identical FRT sites such that the sequence between FRT sites in O replaces the sequence between the corresponding FRT sites of sequence G, thereby yielding a directionally targeted reintegrated new sequence. The new gene in O is now driven off of the P1 promoter in G. The purpose for designing some of the constructs without an ATG start codon on the gene is so that if random integration occurs, there is an extremely low probability of expression of the introduced gene, since in order for this to happen, the fragment would need to integrate behind an endogenous promoter region and in the correct reading frame. This would occur extremely rarely and our data to date have yielded no examples of this happening using a sequence such as O where the contained gene is the easily scorable GUS gene. One requirement for each gene to be constructed in this way (i.e., no ATG on the gene but with the ATG upstream of the FRT site) is the demonstration that the gene can tolerate a fusion of the FRT sequence between the ATG codon and the second codon of the protein. To date this has worked for quite a number but not all genes; in the latter cases the other form of the construct retaining the ATG (for example Q.) could be used. All of the sequences listed above are expected to work in this scheme, some at different frequencies or efficiencies than others.

One problem this strategy addresses is limitations with current transformation approaches, particularly in plants, where delivery of DNA into cells or nuclei and subsequent integration in the genome occurs more or less randomly and unpredictably. This is particularly true with particle bombardment methods; arguments have been made that Agrobacterium-based methods tend to deliver T-DNA border-flanked sequences to more actively transcribed regions of the genome, but beyond that the process is still largely random. Therefore, for commercial product development, large numbers (estimates of >200) of events need to be generated in order to identify one event: a) that expresses at the desired level; b) where the gene product is functional and efficacious; c) which has a simple integration complexity to facilitate breeding; d) which does not contain extraneous sequences posing possible regulatory concerns; e) which maintains stability in expression over generations; f) most importantly, which does not have a negative impact on agronomic performance characteristics when carried through a breeding program involving introgression of the trait into different genetic backgrounds. Resource utilization is very large and so schemes that can markedly reduce the resource demand would be very beneficial to production of larger numbers of desired final products.

EXAMPLE 1

Creation of Novel Non-identical FRT Sites

DNA fragments containing novel FRT sequences were constructed either by synthesizing, annealing and ligating complementary oligonucleotides or by creating primers for PCR amplification (Mullis and Faloona, 1987) of a DNA product containing the new FRT sequence near the 5' end of the PCR product. The newly constructed FRT product includes flanking restriction sites useful for cloning into plant expression units. In general, the 5' end is flanked by an NheI site and a terminal NcoI site. The NcoI site includes the bases ATG, which are advantageously used in newly developed vector constructs as the recognition sequence to initiate an open reading frame. In sequence-based constructs designated noATG/FRT, the NheI site is used for cloning thereby eliminating the upstream ATG in the process. At the 3' end of the FRT sequence, a restriction site is included enabling unique identification of the individual spacer sequences. As specific examples, the wild type FRT site (designated FRT1 here) is cloned with a flanking BglII site, the FRT5 site (spacer TTCAAAAG) (nt 39–46 of SEQ ID NO:3) has a ScaI site, the FRT6 site (spacer TTCAAAAA) (nt 36–49 of SEQ ID NO:4) has an AatII site, and the FRT7 site (spacer TTCAATAA) (nt 36–46 of SEQ ID NO:5) has an SpeI site. The outermost flanking restriction site is an XhoI site and is used to clone a gene of interest into the open reading frame.

The structures and sequences of the FRT sites as designed and/or used in the present invention example are depicted below with positions of restriction sites, repeats and spacer regions indicated.

the ATG start codon to GTG. Ligation of an FRT to the mutated gene sequence at XhoI creates a new open reading frame initiating 5' to the FRT. A second FRT sequence can be cloned downstream of the terminator using a variety of methods including PCR or ligation. The FRT/gene/terminator/FRT unit can then be used to make target or substrate constructs.

Targets are created by inserting a promoter at the NcoI site upstream of the first FRT. This maintains a complete open reading frame of the FRT/gene fusion. These target constructs are for use in transformation experiments to create desirable 'target lines'. Substrate vectors are constructed by cloning with the NheI site to truncate the start codon of the FRT /gene unit, thereby eliminating the proper open reading frame. These substrate vectors are used in experiments designed to retarget a new gene flanked by FRT sites into the corresponding FRT sites previously introduced in the target lines. In either case, to create multiple gene cassettes, additional promoter/gene/terminator units are inserted between the terminator and the second FRT in either target or substrate molecules.

EXAMPLE 3

Demonstration of Functionality of Novel FRT Sites and Requirement for Two Identical Sites for Efficient Recombination of DNA Sequences Positioned between Two FRT Sites Plasmids containing two identical or two different FRT sequences were assayed for efficiency of recombination of sequences between the FRT sites by transformation into 294-FLP, a version of the *E. coli* strain MM294 with FLP recombinase integrated into the lacZ locus (Buchholz et al.

```
FRT1 (SEQ ID NO 2)

NcoI   NheI    Repeat 1       Repeat 2       Spacer     Inverted Repeat   BgIII XhoI 5'      CCATGGCTAGC GAAGTTCCTATTCC GAAGTTCCTATTC TCTAGAAA GTATAGGAACTTC AGATCTCGAG

FRT5 (SEQ ID NO 3)

NcoI   NheI    Repeat 1       Repeat 2       Spacer     Inverted Repeat    ScaI  XhoI 5'      CCATGGCTAGC GAAGTTCCTATTCC GAAGTTCCTATTC TTCAAAAG GTATAGGAACTTC AGTACTCGAG

FRT6 (SEQ ID NO 4)

NcoI   NheI    Repeat 1       Repeat 2       Spacer     Inverted Repeat    AatII  XhoI 5'      CCATGGCTAGC GAAGTTCCTATTCC GAAGTTCCTATTC TTCAAAAA GTATAGGAACTTC AGACGTCCTCGAG

FRT7 (SEQ ID NO 5)

NcoI   NheI    Repeat 1       Repeat 2       Spacer     Inverted Repeat    SpeI   XhoI 5'      CCATGGCTAGC GAAGTTCCTATTCC GAAGTTCCTATTCTTCAATAA GTATAGGAACTTCACTAGTTCTCGAG
```

EXAMPLE 2

Creation of Plant Transformation Vectors Containing Novel Non-identical FRT Sites Based on the design of FRT sites as described above, PCR or standard mutagenesis protocols were used to create an XhoI site overlapping the start of a gene sequence to be used for cloning downstream of the FRT site, thereby converting 1996). Strains were grown overnight at 37° C. with shaking, allowing for constitutive expression of FLP recombinase in the cultures. The plasmid DNA was isolated using standard procedures and digested with restriction enzymes that create novel restriction fragments following FLP mediated recombination. The extent of recombination between FRT sites was estimated by examining banding patterns on an agarose gel. Table 1 summarizes data from the gel analysis.

TABLE 1

| Target Site Combination | Extent of Recombination |
|---|---|
| FRT1 and FRT1 | Complete |
| FRT5 and FRT5 | Extensive, but partially incomplete |
| FRT6 and FRT6 | Complete |
| FRT7 and FRT7 | Complete |
| FRT1 and FRT5 | No recombination |
| FRT1 and FRT6 | No recombination |
| FRT1 and FRT7 | No recombination |
| FRT5 and FRT6 | No recombination |
| FRT5 and FRT7 | No recombination |
| FRT6 and FRT7 | Very small amount of recombination |

The results from these studies indicate that excision of sequences between identical FRT sites occurs with high efficiency in general (FRT5, SEQ ID NO 3, appeared to be less efficient overall than FRT1, SEQ ID NO 2, or the novel FRT6, SEQ ID NO 4, and FRT 7, SEQ ID NO 5, sites). As importantly, recombination with two different FRT sites was absent, or at least undetectable under the conditions of this assay for all combinations but FRT6, SEQ ID NO 4, and FRT7, SEQ ID NO 5, where a small degree of recombination was noted. These data provided strong support for the potential utility of non-identical FRT sites in developing a directional gene integration system. A point to note is that because recombination of sequences between two identical FRT sites can occur with different efficiencies depending on the specific FRT site used (e.g., FRT5, SEQ ID NO 3, in the present experiment), the design of constructs for directional targeted integration may require judicious selection of pairs of FRT sites to optimize for the desired recombination efficiency or to avoid any unwanted recombination.

EXAMPLE 4

Introduction of DNA Sequences Which Include Novel Non-identical FRT Sites into Plant Cells, Generation and Recovery of Stable Transgenic Events ('Target Lines'), Preservation of 'Target Lines' and Regeneration of Plants A number of stable transgenic events carrying FRT target sites were produced. These target lines were generated by introducing one of a series of constructs including, for example, PHP9643, PHP10616, PHP11407, PHP11410, PHP11457, PHP11599, PHP11893 or PHP14220 (See Table 2) into corn cells, either by particle bombardment, as described in Register et al. (1994) *Plant Mol. Biol.* 25:951–961 or via Agrobacterium co-cultivation as described by Heath et al. (1997) Mol. *Plant-Microbe Interact.* 10:22–227; Hiei et al. (1994) *Plant J* 6:271–282 and Ishida et al. (1996) *Nat. Biotech.* 14:745–750, and in U.S. Provisional Application Serial No. 60/045,121 to "Agrobacterium Mediated Sorghum Transformation", filed Apr. 30, 1997, now U.S. application Ser. No. 09/056,418, filed Apr. 7, 1998. All vectors were constructed using standard molecular biology techniques as described for example in Sambrook et al., (1989) *Molecular Cloning: A Laboratory Manual ($2^{nd}$* ed., Cold Spring Harbor Laboratory: Cold Spring Harbor, N.Y.). Table 2 below describes the components within each of the vectors used to create a set of target lines. The assembly strategy was as follows. The first expression unit in each case contains the 2.0 kb PstI fragment of the maize ubiquitin promoter Ubi-1 (Christensen et al. (1992) Plant Mol. Biol. 18:675–689). Downstream of the ubiquitin promoter, varying FRT sequences were inserted using NcoI or other sites that retained the ATG start codon. PHP10616 has the mo-PAT (U.S. Provisional Patent Application Serial No. 60/035,560 to "Methods for Improving Transformation Efficiency", filed Jan. 14, 1997 now U.S. Pat. No. 6,096,947) coding sequence fused in frame at the XhoI site flanking FRT1 (see above, SEQ ID NO:2). PHP11407 and PHP11893 have GFPm-C3 (PCT/US97/ 07688 filed May 1, 1997 from Provisional Application 60/016,345 filed May 1, 1996, now W097/41228) containing the second intron from potato ST-LS1 (Vancanneyt et al. (1990) Mol. Gen. Genet. 220:245–250) fused in frame at the XhoI site of FRT1 and FRT6, respectively. The potato proteinase inhibitor II (PinII) terminator (bases 2 to 310 from An et al. (1989) Plant Cell 1:115–122) was ligated downstream of the coding sequences. PHP10616 has an FRT5 sequence (SEQ ID NO :3) cloned downstream of the PinII terminator.

TABLE 2

| PHP | Upstream-1 | Coding-1 | Downstream-1 | Upstream-2 | Coding-2 | Downstream-2 | Coding-3 | Downstream-3 |
|---|---|---|---|---|---|---|---|---|
| 9643 | Ubiquitin | ATG/FRT1 | | E35S/35S/O'/ADH intron | moPAT | 35S term | NoATG/FRT1/GFP m | pinII, FRT5 |
| 10616 | Ubiquitin | ATG/FRT1/moPAT | pinII, FRT5 | | | | | |
| 11407 | Ubiquitin | ATG/FRT1/GFPm-C3-intron | pinII | Ubiquitin | HM1 | pinII, FRT5 | | |
| 11410 | Ubiquitin | ATG/FRT5 | | E35S/35S/O'/ADH intron | BAR | 35S term, FRT1 | | |
| 11457 | Ubiquitin | ATG/FRT6 | | E35S/35S/O'/ADH intron | BAR | 35S term, FRT1 | | |
| 11599 | Ubiquitin | ATG/FRT6 | | 35S/O'/ADH intron | BAR | 35S term, FRT1 | | |
| 11893 | Ubiquitin | ATG/FRT6/GFPm-C3-intron | pinII | Ubiquitin | HM1 | pinII, FRT1 | | |
| 14220 | Ubiquitin/FRT1 in 5' UTR | FLPm | pinII | Ubiquitin | GFPm | pinII, FRT5 | | |
| | Ubiquitin/FRT1 in intron | FLPm | pinII | Ubiquitin | GFPm | pinII, FRT5 | | |

The second expression units have the maize ubiquitin promoter or alternatively either the enhanced or the standard versions of the cauliflower mosaic virus 35S promoter. The standard 35S promoter includes bases −421 to +2 (from Gardner et al. (1981) Nucl. Acids Res. 9:2871–2888), and the enhanced version has a duplication of bases −421 to −90 upstream of this standard 35S promoter. The 79 bp tobacco mosaic virus leader O' (Gallie et al. (1987) Nucl. Acids Res. 15:3257–3273) is inserted downstream of the 35S promoter followed by the first intron of the maize alcohol dehydrogenase ADH1-S gene (Dennis et al. (1984) Nucl. Acids Res. 12:3983–3990). Coding sequences in these second expression units include either mo-PAT, bar (Thompson et al. (1987) EMBO J. 6:2519–2523), or HM1 (Johal and Briggs, Science 258:985–987) genes followed by either the PinII terminator or the 35S terminator (nucleotides 7487–7639 in Gardner et al. (1981) Nucl. Acids Res. 9:2871–2888). Varying FRT sites are ligated downstream of the terminators as shown in the table. A third expression unit is present in PHP9643 and has an FRT1/GFPm fusion cloned using the flanking NheI site of FRT1 (SEQ ID NO 2) to remove the ATG start codon of GFPm, thereby making it non-functional in the existing construct, but where correct excision of sequences between FRT1 (SEQ ID NO 2) sites can bring the GFPm in frame with the ubiquitin promoter and ATG of the first expression unit, thereby making it functional. Downstream of GFPm is the PinII terminator followed by an FRT5 sequence (SEQ ID NO 3).

PHP9643 was cloned into a pUC derived plasmid backbone. All other vectors were cloned into a pSB11 (See, for example, EPA0672752A1, EPA0604662A1, EPA0687730A1 and U.S. Pat. No. 5,591,616) type plasmid with the expression units contained between the TDNA border sequences. All are oriented with expression unit one adjacent to the right border. The pSB11-based plasmids were integrated into the super binary plasmid pSB1 (See, for example, EPA0672752A1, EPA0604662A1, EPA0687730A1 and U.S. Pat. No. 5,591,616) by homologous recombination between the two plasmids. E. coli strain HB101 containing the pSB11 derivatives was mated with Agrobacterium strain LBA4404 harboring pSB1 to create the cointegrate plasmids PHP10616, PHP11407, PHP11410, PHP11457, PHP11599, PHP11893 and PHP14220 in Agrobacterium (by the method of Ditta et al. (1980) Proc. Natl. Acad. Sci. USA 77:7347–7351). The cointegrates were verified by Agrobacterium resistance to spectinomycin and SalI restriction digests.

Table 2 also includes one example of a vector for creating a target line where the FRT sites are inserted in the maize ubiquitin intron (last entry) as an alternative location for placement of FRT or other target sites.

Following selection of stably transformed events, samples of these target lines were cryopreserved as a supply for future experiments using the approach described by Peterson (see application Ser. No. 08/859,313, now U.S. Pat. No. 6,143,563). For several but not all events, another sample callus from several of the stable transgenic events was grown, transferred onto regeneration medium to induce plantlet formation and plants were subsequently recovered and grown to maturity (Register et al. (1994) Plant Mol. Biol. 25:951–961).

EXAMPLE 5

Demonstration of Functionality of Novel FRT Sites in Plants (A) Excision of DNA sequences between two identical FRT sites, but not when flanked by two non-identical FRT sequences The extent of intra-plasmid recombination was examined in plants using the FRT excision constructs described in Table 3 below. The vectors PHP10968, PHP10998, PHP10969, PHP11272, PHP11243, PHP11244, PHP12140, PHP12141, PHP12156, and PHP 12157 were constructed by ligating the maize Ubiquitin promoter upstream of FRT sequences using NcoI or other sites that maintained the ATG start codon. The FRT sequence was fused in frame at the flanking XhoI site to a GFPm sequence containing a serine to threonine mutation at amino acid residue 65 in the wild type sequence (new sequence termed GFPm-S65T). The pinII terminator was cloned downstream of GFPm. The second expression unit consists of a promoterless FRT, cloned with the 5' flanking NheI site to remove the ATG start codon, fused in frame to the GUS coding sequence (Jefferson et al. (1986) Proc. Natl. Acad. Sci. USA 83: 8447–8451) and followed by the pinII terminator. The vector backbone is a pUC derived plasmid in all cases. Experiments were conducted by bombarding the indicated plasmids into maize cells along with construct PHP5096, which carries a functional expression cassette for FLP protein. PHP5096, the FLPm expression vector that was used in experiments with the excision and substrate vectors, consists of the maize Ubiquitin promoter cloned upstream of the FLPm coding sequence (U.S. patent application Ser. No. 08/972,258 to "Novel Nucleic Acid Sequence Encoding FLP Recombinase" now U.S. Pat. No. 5,929,301) and the pinII terminator in a pUC derived plasmid backbone. In each case, successful excision would remove intervening sequences between the indicated FRT sites thereby bringing an inactive uidA (GUS) gene in frame with and in proximity to the ubiquitin promoter resulting in GUS activity. If excision does not occur, no GUS expression is expected. The results for GUS expression from these experiments are indicated in Table 4 below. In these studies efficient excision occurred only where constructs contained two identical FRT sites. In the case of the FRT6 (SEQ ID NO:4) and FRT7 (SEQ ID NO:5) combination, a small amount of recombination was observed, again emphasizing the need for testing target site combinations and judiciously selecting appropriate combinations for the application.

TABLE 3

| PHP | Upstream-1 | Coding-1 | Downstream-1 | Upstream-2 | Coding-2 | Downstream-2 |
|---|---|---|---|---|---|---|
| 10968 | Ubiquitin | ATG/FRT1/GFPm-S65T | PinII | | noATG/FRT1/GUS | pinII |
| 10998 | Ubiquitin | ATG/FRT5/GFPm-S65T | PinII | | noATG/FRT5/GUS | pinII |
| 11272 | Ubiquitin | ATG/FRT6/GFPm-S65T | PinII | | noATG/FRT6/GUS | pinII |
| 12157 | Ubiquitin | ATG/FRT7/GFPm-S65T | PinII | | noATG/FRT7/GUS | pinII |
| 10969 | Ubiquitin | ATG/FRT1/GFPm-S65T | PinII | | noATG/FRT5/GUS | pinII |
| 11243 | Ubiquitin | ATG/FRT1/GFPm-S65T | PinII | | noATG/FRT6/GUS | pinII |
| 12140 | Ubiquitin | ATG/FRT1/GFPm-S65T | PinII | | noATG/FRT7/GUS | pinII |
| 11244 | Ubiquitin | ATG/FRT5/GFPm-S65T | PinII | | noATG/FRT6/GUS | pinII |

TABLE 3-continued

| PHP | Upstream-1 | Coding-1 | Downstream-1 | Upstream-2 | Coding-2 | Downstream-2 |
|---|---|---|---|---|---|---|
| 12141 | Ubiquitin | ATG/FRT5/GFPm-S65T | PinII | | noATG/FRT7/GUS | pinII |
| 12156 | Ubiquitin | ATG/FRT6/GFPm-S65T | PinII | | noATG/FRT7/GUS | pinII |
| 12933 | Ubiquitin/FRT1 in 5' UTR | GFPm-S65T | PinII | FRT1 in 5' UTR/Ubi intron | GUS | pinII |
| 14076 | Ubiquitin/FRT1 in intron | AHAS | PinII | FRT1 in Ubi intron | GUS | pinII |
| 14053 | Ubiquitin/FRT1 in intron | AHAS | PinII | FRT5 in Ubi intron | GUS | pinII |
| 14086 | Ubiquitin/FRT1 in intron | AHAS | PinII | FRT6 in Ubi intron | GUS | pinII |

TABLE 4

| Plasmid | Recombination tested between | GUS expression |
|---|---|---|
| PHP10968 | FRT1 and FRT1 | +++ |
| PHP10998 | FRT5 and FRT5 | ++ |
| PHP11272 | FRT6 and FRT6 | +++ |
| PHP12157 | FRT7 and FRT7 | +++ |
| PHP9643 | FRT1 and FRT5 | − |
| PHP11243 | FRT1 and FRT6 | − |
| PHP12140 | FRT1 and FRT7 | − |
| PHP11244 | FRT5 and FRT6 | − |
| PHP12141 | FRT5 and FRT7 | − |
| PHP12156 | FRT6 and FRT7 | + |

B) Transient integration of a second DNA sequence flanked by two non-identical FRT sequences into plant cells Summarized in Table 5 below are data from experiments in which target lines created using the plasmids described in Table 2 were bombarded with a substrate plasmid containing a GUS reporter gene flanked by the corresponding FRT sites used in the target constructs. This experiment measured the ability to detect transient GUS expression shortly after introduction of the substrate plasmid. Since there is no promoter in front of the first coding sequence in the substrate plasmids, random integration, unless occurring in frame behind an appropriate regulatory sequence elsewhere in the genome, would not result in GUS expression. This assay system then evaluates the ability to target FRT-flanked genes into FRT sites in the genome. In general, FRT substrate vectors (Table 6) are constructed as promoterless FRT/gene fusions cloned using the 5' flanking NheI site of the FRT to remove the ATG start codon. Genes fused in frame to the FRT with the flanking XhoI site include one of several scorable or selectable marker genes such as aadA (Svab et al. (1990) Plant Mol. Biol. 14: 197–205), uidA, GFPm, GFPm-C3/intron or bar and are followed by a pinII terminator. In some cases (PHP10259, PHP10603, PHP11561, and PHP11633), plasmids contain a single expression unit and the second heterologous FRT site is cloned downstream of the pinII terminator. Substrate plasmids PHP10859, PHP10997, PHP1 1204, PHP1 1699, and PHP12190 have in addition to the first expression unit described above, a second unit consisting of the maize ubiquitin promoter, the enhanced 35S promoter or a chimeric promoter consisting of the 35S enhancer region cloned upstream of a synthetic core promoter termed Rsyn7 (U.S. Pat. No. 6,072,050 which is a continuation in part of U.S. patent application Ser. No. 08/661,601 filed Jun. 11, 1996 now abandoned) cloned upstream of either the HM1, aadA, GUS, or bar coding sequences and the pinII terminator. A heterologous FRT is inserted downstream of the second terminator. Finally, PHP 11003 and PHP 11809 contain three expression units. The first unit is a promoterless noATG/FRT/gene fusion as described above, the second unit contains either the chimeric 35S enhancer/Rsyn7 promoter described above or the ZmdJ1 promoter (Baszczynski et al. (1997) Maydica 42:189–201) cloned upstream of the GUS coding sequence and the pinII terminator. The third expression unit consists of the maize ubiquitin promoter cloned upstream of the HM1 coding sequence, pinII terminator and a heterologous FRT sequence. All FRT substrate vectors are cloned into a pUC derived plasmid backbone. Details of the components of these vectors are described in Table 6. Also listed in Table 6 are two vectors with alternative placement of FRT sites in the ubiquitin 5' UTR or intron.

TABLE 5

| # of GUS Spots | PHP9643 (n = 74) | PHP11147 (n = 127) | PHP11410 (n = 32) | PHP11407 (n = 38) | PHP11457 (n = 113) |
|---|---|---|---|---|---|
| no spots | 17.57% | 3.15% | 6.25% | 2.63% | 7.96% |
| 1–25 | 22.97% | 48.03% | 62.50% | 10.53% | 27.43% |
| 26–100 | 31.08% | 37.80% | 18.75% | 18.42% | 32.74% |
| 101–200 | 14.86% | 8.66% | 12.50% | 57.89% | 27.43% |
| too many to count | 13.51% | 2.36% | 0.00% | 10.53% | 4.42% |

TABLE 6

| PHP | Coding-1 | Downstream-1 | Upstream-2 | Coding-2 | Downstream-2 | Upstream-3 | Coding-3 | Downstream-3 |
|---|---|---|---|---|---|---|---|---|
| 10259 | NoATG/FRT1/aadA | pinII, FRT5 | | | | | | |
| 10603 | NoATG/FRT1/GUS | pinII, FRT5 | | | | | | |
| 10859 | NoATG/FRT1/GFPm | PinII | Ubiquitin | HM1 | pinII, FRT5 | | | |
| 10997 | NoATG/FRT5/GUS | PinII | Ubiquitin | aadA | pinII, FRT5 | | | |
| 11003 | NoATG/FRT1/GFPm | PinII | E35S/Rsyn7/O'/ADH intron | GUS | pinII | Ubiquitin | HM1 | pinII, FRT5 |
| 11204 | NoATG/FRT1/BAR | PinII | E35S/Rsyn7/O'/ADH intron | GUS | pinII, FRT5 | | | |
| 11561 | NoATG/FRT6/GUS | pinII, FRT1 | | | | | | |
| 11633 | NoATG/FRT5/GUS | pinII, FRT1 | | | | | | |

TABLE 6-continued

| PHP | Coding-1 | Downstream-1 | Upstream-2 | Coding-2 | Downstream-2 | Upstream-3 | Coding-3 | Downstream-3 |
|---|---|---|---|---|---|---|---|---|
| 11699 | NoATG/FRT6/ GFPm-C3-intron | PinII | Ubiquitin | HM1 | pinII, FRT1 | | | |
| 11809 | NoATG/FRT6/ GFPm-C3-intron | PinII | F3.7 | GUS | pinII | Ubiquitin | HM1 | pinII, FRT1 |
| 12190 | NoATG/FRT1/GUS | PinII | E35S/35S/O'/ADH intron | BAR | pinII, FRT5 | | | |
| | | | Ubiquitin/FRT1 in 5' UTR | HM1 | pinII | E35S/35S/O'/ADH intron | BAR | pinII, FRT5 |
| | | | Ubiquitin/FRT1 in intron | HM1 | pinII | E35S/35S/O'/ADH intron | BAR | pinII, FRT5 |

Results in Table 5 indicate that the frequency and level of GUS expression varies among different events, as might be predicted for genes inserted in different positions in the genome. The prediction is that once a high frequency, high expressing line is identified, that the expression of genes subsequently introduced into those same sites will also be higher than in other lower expressing events.

C) Stable integration of a second DNA sequence flanked by two non-identical FRT sequences into plant cells A subset of the stable transgenic "target lines" described in example 4 above was used in experiments aimed at stably retargeting into these primary target lines a new gene flanked by the same FRT sites used in the target lines and cloned in a second construct 'substrate' plasmid. Table 7 lists the constructs contained in the primary target lines (from Table 2), the FRT sites contained in these lines and the substrate plasmids (from Table 6) that were subsequently retargeted into the target lines.

Table 8 presents data from stable transgenic events which demonstrate successful and reproducible targeting of introduced sequences to previously created genomic target sites. The data shown are for 18 independent target lines, each retargeted with a promoterless GUS construct. Since the bar gene was concurrently introduced on the same plasmid, the proportion of GUS expressing events from the total events recovered on bialophos selection provides a measure of retargeting frequency relative to random integration.

TABLE 7

| Target construct | FRT sites | Substrates being evaluated |
|---|---|---|
| PHP9643 | 1/1/5 | 10603, 10259, 10859, 10997, 11003 |
| PHP11147 | 1/5 | 10603, 10859, 11003 |
| PHP11407 | 1/5 | 10603, 11204, 12190 |
| PHP11410 | 5/1 | 11633 |
| PHP11457 | 6/1 | 11561, 11699, 11809 |
| PHP11893 | 6/1 | Experiments in progress |

TABLE 8

| Target Line | # of Random Events | # of Targeted Events | Targeting Frequency (%) |
|---|---|---|---|
| A | 13 | 1 | 7.1 |
| B | 14 | 1 | 6.7 |
| C | 108 | 14 | 11.5 |
| D | 18 | 1 | 5.3 |
| E | 14 | 2 | 12.5 |
| F | 9 | 1 | 10.0 |
| G | 65 | 1 | 1.5 |
| H | 63 | 9 | 12.5 |

TABLE 8-continued

| Target Line | # of Random Events | # of Targeted Events | Targeting Frequency (%) |
|---|---|---|---|
| I | 71 | 6 | 7.8 |
| J | 15 | 1 | 6.3 |
| K | 33 | 9 | 21.4 |
| L | 19 | 2 | 9.5 |
| M | 8 | 1 | 11.1 |
| N | 12 | 1 | 7.7 |
| O | 29 | 4 | 12.1 |
| P | 43 | 4 | 8.5 |
| Q | 16 | 3 | 15.8 |
| R | 4 | 1 | 20.0 |
| S | 12 | 1 | 7.7 |
| T | 10 | 1 | 9.1 |
| U | 1 | 2 | 66.7 |

EXAMPLE 6

Evaluation of Impact of Introduced FRT Sequences on Plant Development, Gene Expression and Agronomic Performance Initial evaluation of the impact of the introduced sequences on plant growth and gene expression is conducted in the greenhouse by making regular observations through to pollination and seed set. Plants are both selfed and crossed to other genotypes to obtain T1 seed for subsequent greenhouse and field evaluation. For gene expression evaluation, both qualitative and quantitative data are collected and analyzed. T1 seeds from transgenic events which give acceptable or desirable levels of expression and which show no significant negative impact on plant development (e.g., have normal developmental morphology, are male and female fertile, etc.) are then grown in managed field plots along with non-transgenic control plants, and standard agronomic performance data is collected and evaluated.

EXAMPLE 7

Conversion of an Introduced Functional FRT Sequence into a Second Non-identical Functional FRT Sequence The approach taken here to develop a method for converting between different FRT sites for use in various applications is based on the previously described 'chimeraplasty' strategy for making specific targeted nucleotide modifications at a specified extrachromosomal or genomic target sequence in animal cells (Yoon et al. (1996) Proc. Natl. Acad. Sci. 93:2071–2076; Cole-Strauss et al. (1996) Science 273:1386–1389). This capability in plants, as demonstrated recently in our laboratories and described in U.S.

Patent Application Serial No. 60/065,628, filed Nov. 18, 1997, is beneficial to extending the potential use of the present invention for broader application. The proposed use of this 'chimeraplasty' technology in the present invention would be to target and modify nucleotides in one FRT site of a pair of non-identical FRT sites flanking a DNA sequence of interest in a way that then makes the two FRT sites identical. Subsequent or concurrent expression of FLP recombinase in cells with these FRT site modifications would lead to excision of the sequences between these now identical FRT sites, thereby removing specifically the undesirable DNA sequences from the previously created stable transgenic event containing those sequences. An application of this approach would be for example in the case of a selectable marker which is required during initial steps of a breeding or backcrossing program to maintain and select for preferred individual plants, but which is not desired in the final product.

A) Vector design and construction for testing chimeraplasty-based FRT site conversion The target vectors for evaluating this FRT site modification strategy are shown generically below, where P1 and P2 represent two different promoters, G1 and G2 represent two genes, and T1 and T2 represent two terminator regions; these regions are shown as white boxes. Different FRT sites are indicated and shown as dark boxes. One version of the construct incorporates a third unique FRT site downstream of the second gene and is used to evaluate whether the targeted conversion, in this case, of FRT5 to FRT6 (SEQ ID NO 4), also results in conversion of the downstream FRT1 (SEQ ID NO 2) site to an FRT6 (SEQ ID NO 4) site. In the former case, expression of the downstream gene (G1) should be detected, while if the conversion is not specific to FRT5 (SEQ ID NO 3) and the FRT1 (SEQ ID NO 2) site is converted also, then both gene activities will be lost. For the specific examples used here P1 is the maize ubiquitin promoter, P2 is the enhanced CaMV 35S promoter, G1 is the uidA (GUS) gene, G2 is the bar gene, and T1 and T2 are pinII terminators. It is understood that based on the various descriptions of vector constructs earlier in this application, a variety of different promoters, genes, terminators or DNA sequences or FRT sites could be used in practicing this component method. The DNA cassettes as shown below could be assembled into either a pUC-based plasmid for direct DNA delivery methods (such as particle bombardment) or into a binary vector for Agrobacterium-based transformation as described previously.

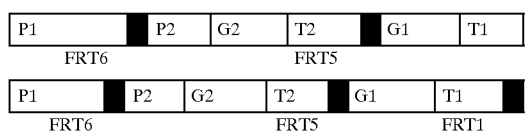

B) Design of chimeric oligonucleotide molecules for chimeraplasty-based targeted conversion of an FRT site Shown below are specific examples of chimeric molecules that would be used to modify a single nucleotide so as to convert the FRT5 (SEQ ID NO 3) site to an FRT6 (SEQ ID NO 4) site in constructs as described above. Both the linear sequence of these chimeric molecules as well as the predicted active form of the molecule (based on the Yoon et al. and Cole-Strauss et al. publications above) are shown. DNA residues are represented in upper case, RNA residues in lower case, and the site to be modified (a single nucleotide difference between FRT5, SEQ ID NO 3, and FRT6, SEQ ID NO 4) is underlined and in bold. Two examples of chimeras are presented below differing in the number of residues downstream of the FRT5 (SEQ ID NO 4) site that would be included in the chimeric molecule design and which would thus determine the specificity to the target sequence.

1. Chimeric oligonucleotide linear sequence (sequence includes six target-specific residues downstream of the FRT site being modified in the target construct and should convert only this single specific FRT5, SEQ ID NO 3, site to an FRT6, SEQ ID NO 4, site)

```
CCTATTCTTCAAAAAGTATAGGAACTTCAGTACTTTTTaguacugaaguuCCTA  (SEQ ID NO:6)

TACTTTuugaagaauaggGCGCGTTTTCGCGC-3'
```

Active oligonucleotide conformation of SEQ ID NO:6

```
        TGCGCG--ggauaagaaguuTTTCATATCCuugaagucaugaT
      T                                            T
      T                                            T
        TCGCGC   CCTATTCTTCAAAAAGTATAGGAACTTCAGTACTT
             3' 5'
```

2. Chimeric oligonucleotide linear sequence (sequence contains residues specific to only sequences in the FRT site and so should convert any FRT5, SEQ ID NO3, site in a target molecule to an FRT6, SEQ ID NO 4, site)

```
5'-TATTCTTCAAAAAGTATAGGAACTTCTTTTgaaguuccuaTACTTTuugaaga   (SEQ ID NO:7)

auaGCGCGTTTTCGCGC-3'
```

Active oligonucleotide conformation of SEQ ID NO:7

```
        TGCGCG--auaagaaguuTTTCATauccuugaagT
      T                                    T
      T                                    T
        TCGCGC   TATTCTTCAAAAAGTATAGGAACTTCT
             3' 5'
```

Vector constructions and chimeric oligonucleotide molecules as described above were generated and used in experiments.

C) Demonstration of conversion from one FRT site to another

Stable transgenic maize lines are generated with the constructs as described above or with other related ones by transforming in the constructs and selecting on bialophos as described before. Tissues to be used for chimera delivery are transferred onto non-bialophos-containing media and the chimeric oligonucleotides are delivered into cells of these stable events by particle bombardment, together with co-delivery of PHP5096 which carries a functional FLP recombinase expression cassette. In control experiments, only chimeric molecules or only PHP5096 are delivered. After sufficient time for cells to recover without bialophos selection, samples of the bombarded events are evaluated for GUS expression. For those bombarded events containing the construct with the downstream FRT1 (SEQ ID NO 2) site which do not show GUS expression, an equivalent sample of cells are plated and grown on medium with or without bialophos selection to assess sensitivity to the chemical. If the chimeric molecules are specific for modifying only the FRT5 (SEQ ID NO 3) site, then no differences in number and growth of cells should be observed between treatments with or without selection. Otherwise, reduced growth and recovery should be noted.

D) Molecular verification of stable conversion of FRT sites

DNA from those samples that exhibit GUS expression is isolated, amplified by PCR if necessary, and sequenced by standard methods through the region corresponding to the predicted nucleotide conversion. A sufficient stretch of DNA is sequenced to cover the entire originally introduced region of DNA so as to confirm correct and specific conversion. Using standard methods for PCR, Southern analysis and/or sequencing of GUS expressing and non-expressing samples establishes the presence or absence of specific DNA fragments prior to and following chimeric molecule and FLP recombinase delivery, and thus substantiates the visual and biochemical observations made above.

E) Utility of chimeraplasty-based FRT site conversion in a transgene stacking strategy for plants Described in FIG. 1 is one potential strategy for combining or stacking multiple desired transgenes at one genomic location using the non-identical FRT-based system of the present invention. While stacking of genes can be achieved without the use of the targeted FRT conversion method described in this example 7, this latter method extends the capabilities of the system by allowing in vivo conversion of FRT sites to create new sites, rather than re-introducing new FRT sites by transformation. In the diagram of FIG. 1, an FRT site with an asterisk beside it indicates that it was initially created to be non-functional with respect to recombination between it and the equivalent FRT site without an asterisk, but which upon conversion with the chimeraplasty-based approach described herein renders it capable of recombination with its equivalent non-asterisk counterpart. In the specific example presented in the figure, this would facilitate for example removal of a selectable marker either to no longer have it present, or to allow one to re-use the selectable marker in future transformations. Thus this method also provides a mechanism to recycle selectable markers, as is possible in using the FRT system of the present invention alone.

Discussion

To date in plants, the major application of the FLP/FRT system has been for DNA excision (Lyznik et al. (1993) *Nucleic Acids Res.* 21:969–975). For example, a gene such as a selectable marker flanked by FRT sites is first introduced into plant cells by one of several transformation approaches, and stable transgenic events or plants are recovered via appropriate selection. Then in order to eliminate the selectable marker gene, FLP protein is expressed in the cells either transiently by introducing a plasmid carrying a FLP expression cassette, stably following integration of an introduced FLP expression cassette, or by crossing plants carrying the FRT-flanked selectable marker gene with plants carrying sequences for and expressing active FLP protein (U.S. patent application Ser. No. 08/972,258 to "Novel Nucleic Acid Sequence Encoding FLP Recombinase").

A major problem associated with developing the FLP/FRT system for integrating genes into animals or plants stems from the fact that the recombination reaction catalyzed by yeast FLP recombinase is a reversible process (Sadowski (1995) in *Progress in Nucleic Acid Research and Molecular Biology* 51:53–91). For example, following introduction of a DNA sequence flanked by similarly oriented FRT sites into plant cells in the presence of actively expressing FLP recombinase, recombination should lead to insertion of the new DNA sequences at the endogenous FRT site. However, with continued expression of FLP enzyme, the reverse reaction would lead to re-excision of the introduced sequences because of recombination between the identical FRT sites. Since the reaction is reversible, integration and excision can repeatedly continue towards equilibrium. As cells divide and the DNA substrate concentration per cell decreases, the probability of integration decreases, such that in general, as long as active FLP protein is expressed the reaction will be driven towards the non-integrated state. To favor integration, a situation must be established which precludes re-excision once integration occurs. A number of strategies have been suggested, including limiting the duration of activity of FLP recombinase through inducible expression or by directly introducing FLP protein or RNA into cells (Sadowski (1995) *Progress on Nucleic Acid Research and Molecular Biology* 51:53–91), but to date no routine non-random integration system has been established for plants.

The present invention describes the development of a useful new gene targeting system for plants which utilizes the yeast FLP recombinase or a modified FLP recombinase designed to work more efficiently in certain plant species and novel non-identical FRT sites which can be used for directional non-reversible DNA integration. Additionally, described herein is a novel use of accessory technologies such as 'chimeraplasty' permitting in vivo or in vitro modification of DNA sequences, such as FRT sites to further extend the utility of the system. Data provided demonstrate the successful stable integration of DNA sequences between two previously introduced non-identical FRT sites in maize. We show also that the DNA sequences between the FRT sites can be subsequently replaced by a second DNA sequence flanked by the same FRT sites as the first. Together these results demonstrate that it is possible to introduce and recover pairs of non-identical FRT sites at certain genomic locations, that one can select desirable or preferred genomic locations for expressing DNA sequences of interest, and that these selected locations can be used to re-target other DNA sequences of interest. Apart from the obvious benefits of being able to integrate genes into the genome of plants, the present invention provides a means for facilitating the introduction of novel genes or DNA sequences into genomic locations previously determined to be particularly beneficial for gene integration from the perspective of providing suitable levels of stable expression of the introduced gene(s) and not exhibiting deleterious impacts on agronomic characteristics including yield. In addition the invention provides a system whereby integration of two or more genes can be targeted to the same genomic location, providing a mechanism for 'gene stacking'. These stacked genes can then be maintained and managed as a closely linked pair of traits in breeding programs. Thus this invention also provides an improved method for introducing, maintaining and breeding multiple genetic traits of interest, including agronomic traits, commercially important genes or other heterologous gene products.

The invention further proposes to use the non-recombination feature of non-identical FRT sites to allow creation of a set of 'parental' lines, which are initially well-characterized for all the desired expression and performance parameters described above. These lines then serve as the basis for introduction of new traits into the same pre-defined sites in the genome where the initial genes were introduced. Many fewer events would need to be generated, since integration would preferentially occur in sites shown to express well and have minimal negative impact on performance.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for reducing the complexity of integration of transgenes in a genome of a plant cell, said method comprising:
   a) transforming plant cells with a transfer cassette flanked by or comprising a first and a second recombination site, wherein said first and said second recombination sites are non-identical, wherein said transfer cassette further comprises a nucleotide sequence of interest and, wherein said plant cells' genomes comprise a target site comprising the first and the second non-identical recombination sites of said transfer cassette;
   b) providing a recombinase that recognizes and implements recombination at the non-identical recombination sites; and
   c) selecting the plant cells having reduced complexity of integrated transgenes in their genome, wherein said reduced complexity comprises the integration of the transfer cassette at the target site.

2. The method of claim 1, wherein providing the recombinase comprises integrating in the genome of said plant cells a nucleotide sequence encoding said recombinase.

3. The method of claim 1, wherein the transfer cassette further comprises at least one additional coding region operably linked to a promoter that drives expression in the plant cells.

4. The method of claim 3, wherein said additional coding region encodes a recombinase that facilitates recombination between the first and the second recombination sites of the transfer cassette and the target site.

5. The method of claim 1, wherein said first and said second non-identical recombination sites are selected from the group consisting of an FRT, a mutant FRT, a LOX, and a mutant LOX site.

6. The method of claim 5, wherein said first and said second non-identical recombination sites are an FRT site and a mutant FRT site.

7. The method of claim 1, wherein providing said recombinase comprises genetically transforming said plant cells with an expression cassette comprising a nucleotide sequence encoding said recombinase.

8. The method of claim 5, wherein said recombinase is FLP.

9. The method of claim 8, wherein said FLP has been synthesized using maize preferred codons.

10. The method of claim 5, wherein said mutant FRT site is FRT 5 (SEQ ID NO: 3), FRT 6 (SEQ ID NO: 4), or FRT 7 (SEQ ID NO: 5).

11. The method of claim 1, wherein said plant cells are from a monocot.

12. The method of claim 11, wherein said monocot is maize.

13. The method of claim 1, wherein said plant cells are from a dicot.

14. The method of claim 13, wherein said dicot is canola, Brassica, soybean, sunflower, or cotton.

15. The method of claim 5, wherein said recombinase is Cre.

16. The method of claim 15, wherein said Cre recombinase has been synthesized using maize preferred codons.

17. The method of claim 1, wherein said plant cells are in a plant.

18. A method for reducing the complexity of integration of transgenes in a genome of a plant cell, said method comprising:
   a) transforming plant cells with a transfer cassette flanked by or comprising a first and a second recombination site, wherein said first and said second recombination sites are non-identical, said transfer cassette further comprising a nucleotide sequence of interest, and said plant cells' genomes comprise a target site comprising the first and the second non-identical recombination sites of said transfer cassette;
   b) providing a recombinase that recognizes and implements recombination at the non-identical recombination sites; and
   c) selecting the plant cells having reduced complexity of integrated transgenes, wherein the transfer cassette is integrated at the target site and having a targeting frequency of the transfer cassette to the target site relative to total genomic integration of the transfer cassette between 1.5% to 66.7%.

19. The method of claim 18, wherein the targeting frequency of the transfer cassette to the target site relative to total genomic integration of the transfer cassette is between 10% to 20%.

20. The method of claim 18, wherein the targeting frequency of the transfer cassette to the target site relative to total genomic integration of the transfer cassette is between 20% to 66.7%.

21. The method of claim 18, wherein the targeting frequency of the transfer cassette to the target site relative to total genomic integration of the transfer cassette is between 1.5% to 10%.

22. The method of claim 18, wherein providing the recombinase comprises integrating in the genome of said plant cells a nucleotide sequence encoding said recombinase.

23. The method of claim 18, wherein the transfer cassette further comprises at least one additional coding region operably linked to a promoter that drives expression in a plant cell.

24. The method of claim 23, wherein said additional coding region encodes a recombinase that facilitates recombination between the first and the second recombination sites of the transfer cassette and the target site.

25. The method of claim 18, wherein said first and said second non-identical recombination sites are selected from the group consisting of an FRT, a mutant FRT, a LOX, and a mutant LOX site.

26. The method of claim 25, wherein said first and said second non-identical recombination sites are an FRT site and a mutant FRT site.

27. The method of claim 18, wherein providing said recombinase comprises genetically transforming said plant cells with an expression cassette comprising a nucleotide sequence encoding said recombinase.

28. The method of claim 25, wherein said recombinase is FLP.

29. The method of claim 28, wherein said FLP recombinase has been synthesized using maize preferred codons.

30. The method of claim 25, wherein said mutant FRT site is FRT 5 (SEQ ID NO: 3), FRT 6 (SEQ ID NO: 4), or FRT 7 (SEQ ID NO: 5).

31. The method of claim 18, wherein said plant cells are from a monocot.

32. The method of claim 31, wherein said monocot is maize.

33. The method of claim 18, wherein said plant cells are from a dicot.

34. The method of claim 33, wherein said dicot is canola, Brassica, soybean, sunflower, or cotton.

35. The method of claim 25, wherein said recombinase is Cre.

36. The method of claim 35, wherein said Cre recombinase has been synthesized using maize preferred codons.

37. The method of claim 18, wherein said plant cells are in a plant.

* * * * *

UNITED STATES PATENT AND TRADEMARK OFFICE
CERTIFICATE OF CORRECTION

PATENT NO.     : 6,573,425 B1
DATED          : June 3, 2003
INVENTOR(S)    : Baszczynski et al.

It is certified that error appears in the above-identified patent and that said Letters Patent is hereby corrected as shown below:

Title page,
Item [56], References Cited, FOREIGN PATENT DOCUMENTS, insert the following:
-- WO WO 97/47758    12/1997 --;
OTHER PUBLICATIONS, insert the following:
-- Umlauf et al., The Functional Significance of DNA Sequence Structure in a Site-Specific Genetic Recombination Reaction, EMBO J. 1988, pp. 1845-1852, Vol. 7(6). --.

Column 20,
Line 13, "PHP1 1204" should read -- PHP 11204 --; and
"PHP1 1699" should read -- PHP 11699 --.

Column 30,
Lines 62-63, "the plant cells" should read -- a plant cell --.

Signed and Sealed this

Fourteenth Day of October, 2003

JAMES E. ROGAN
*Director of the United States Patent and Trademark Office*

SEQUENCE LISTING

```
<160> NUMBER OF SEQ ID NOS: 7

<210> SEQ ID NO 1
<211> LENGTH: 34
<212> TYPE: DNA
<213> ORGANISM: Saccharomyces cerevisiae
<220> FEATURE:
<223> OTHER INFORMATION: (14)...(21) spacer region

<400> SEQUENCE: 1
gaagttccta ttctctagaa agtataggaa cttc                                 34

<210> SEQ ID NO 2
<211> LENGTH: 69
<212> TYPE: DNA
<213> ORGANISM: Unknown
<220> FEATURE:
<223> OTHER INFORMATION: (39)...(46) spacer region
<223> OTHER INFORMATION: Description of Unknown Organism:Constructed by
      synthesizing, annealing and ligating complementary
      oligonucleotides, or by creating primers for PCR
      amplifications

<400> SEQUENCE: 2
ccatggctag cgaagttcct attccgaagt tcctattctc tagaaagtat aggaacttca     60
gatctcgag                                                            69

<210> SEQ ID NO 3
<211> LENGTH: 69
<212> TYPE: DNA
<213> ORGANISM: Unknown
<220> FEATURE:
<223> OTHER INFORMATION: Description of Unknown Organism:Constructed by
      synthesizing, annealing and ligating complementary
      oligonucleotides or by creating primers for PCR
      amplifications
<223> OTHER INFORMATION: (39)...(46) spacer region

<400> SEQUENCE: 3
ccatggctag cgaagttcct attccgaagt tcctattctt caaaaggtat aggaacttca     60
gtactcgag                                                            69

<210> SEQ ID NO 4
<211> LENGTH: 72
<212> TYPE: DNA
<213> ORGANISM: Unknown
<220> FEATURE:
<223> OTHER INFORMATION: Description of Unknown Organism:Constructed by
      synthesizing, annealing and ligating complementary
```

```
         oligonucleotides, or by creating primers for PCR
         amplifications
<223> OTHER INFORMATION: (36)...(49) spacer region

<400> SEQUENCE: 4
ccatggctag cgaagttcct attccgaagt tcctattctt caaaaagtat aggaacttca    60
gacgtcctcg ag                                                       72

<210> SEQ ID NO 5
<211> LENGTH: 72
<212> TYPE: DNA
<213> ORGANISM: Unknown
<220> FEATURE:
<223> OTHER INFORMATION: Description of Unknown Organism:Constructed by
      synthesizing, annealing and ligating complementary
      oligonucleotides or by creating primers for PCR
      amplification
<223> OTHER INFORMATION: (39)...(46) spacer region

<400> SEQUENCE: 5
ccatggctag cgaagttcct attccgaagt tcctattctt caataagtat aggaacttca    60
ctagttctcg ag                                                       72

<210> SEQ ID NO 6
<211> LENGTH: 86
<212> TYPE: DNA
<213> ORGANISM: Artificial Sequence
<220> FEATURE:
<223> OTHER INFORMATION: Description of Combined DNA/RNA Molecule:
      chimericoligonucleotide
<223> OTHER INFORMATION: Description of Artificial Sequence:
      oligonucleotide sequence

<400> SEQUENCE: 6
cctattcttc aaaaagtata ggaacttcag tactttttag uacugaaguu cctatactttt   60 uugaagaaua gggcgcgttt tcgcgc                                        86

<210> SEQ ID NO 7
<211> LENGTH: 70
<212> TYPE: DNA
<213> ORGANISM: Artificial Sequence
<220> FEATURE:
<223> OTHER INFORMATION: Description of Artificial Sequence:
      oliognucleotide sequence

<400> SEQUENCE: 7
tattcttcaa aagtatagg aacttctttt gaaguuccua tactttuuga agaauagcgc    60
gttttcgcgc                                                          70
```